United States Patent [19]

Uchikawa et al.

[11] Patent Number: 5,156,836
[45] Date of Patent: Oct. 20, 1992

[54] HAIR REVITALIZING TONIC COMPOSITION

[75] Inventors: Keiichi Uchikawa; Kiyoshi Miyazawa; Jotaro Nakanishi; Akihiro Ishino, all of Yokohama, Japan

[73] Assignee: Shiseido Company Ltd., Tokyo, Japan

[21] Appl. No.: 505,123

[22] Filed: Apr. 3, 1990

Related U.S. Application Data

[63] Continuation-in-part of Ser. No. 392,622, May 24, 1989, abandoned.

[30] Foreign Application Priority Data

Oct. 2, 1987 [JP] Japan ................... 62-249132
Jan. 14, 1988 [JP] Japan ..................... 63-6233

[51] Int. Cl.⁵ ........................................ A61K 7/075
[52] U.S. Cl. .................................. 424/70; 424/71
[58] Field of Search ............... 424/70; 252/547; 514/644, 788

[56] References Cited

U.S. PATENT DOCUMENTS

| | | | |
|---|---|---|---|
| 3,098,794 | 7/1963 | Dohr et al. | 424/70 X |
| 3,449,430 | 6/1969 | Dohr et al. | 424/70 X |
| 4,033,895 | 7/1977 | Gerstein | 424/70 X |
| 4,210,654 | 7/1980 | Bauer et al. | 514/644 X |
| 4,263,178 | 4/1981 | Guth | 424/70 X |

FOREIGN PATENT DOCUMENTS

| | | | |
|---|---|---|---|
| 133905 | 3/1985 | European Pat. Off. | 424/70 |
| 168719 | 1/1986 | European Pat. Off. | 424/70 |
| 54-49335 | 4/1979 | Japan . | |
| 60-25910 | 2/1985 | Japan . | |
| 61-37717 | 2/1986 | Japan . | |

*Primary Examiner*—Thurman K. Page
*Attorney, Agent, or Firm*—Sprung Horn Kramer & Woods

[57] ABSTRACT

A hair revitalizing tonic having an excellent hair loss prevention and hair revitalizing effect comprising (1) an amine oxide or (2) an amine oxide and an anionic surfactant formulated therein.

6 Claims, No Drawings

HAIR REVITALIZING TONIC COMPOSITION

CROSS REFERENCE TO RELATED APPLICATION

This application is a continuation-in-part of application Ser. No. 392622 filed on May 24, 1989, now abandoned, based upon an international application PCT/JP88/00739 filed on Jul. 22, 1988.

BACKGROUND OF THE INVENTION

1. Field of the Invention

The present invention relates to a hair revitalizing tonic composition having an excellent hair loss preventive effect and hair revitalizing effect.

2. Description of the Related Art

In the prior art, the causes of hair loss from the head are considered to be (1) an activation of male hormones at organs such as hair roots, and of the sebum gland, (2) an insufficient circulation of blood to hair follicles (3) an abnormal and excessive secretion of sebum, and the formation of peroxides, among others.

Accordingly, compounds having the action of removing or alleviating the above-mentioned causes are usually formulated in the hair revitalizing tonic compositions of the prior art.

For example, vitamins such as vitamin E, vasodilators such as Swertia japonica extract, antiinflammatory agents such as hinokitiol, female hormone agents such as estradiol, and skin function promotors such as cepharanthine are formulated for a prophylaxis and therapy of alopecia.

Nevertheless, the mechanism of hair loss and hair generation is complicated, and a satisfactory hair loss prevention and hair revitalizing effect can be obtained only by inhibiting the activation of male hormones or increasing the circulation of blood to hair follicles, according to the hair revitalizing tonic compositions of the prior art.

SUMMARY OF THE INVENTION

Accordingly, an object of the present invention is to solve the above problems of the prior art and provide a hair revitalizing tonic composition having an excellent hair loss prevention effect and hair revitalization effect.

Another object of the present invention is to provide a hair revitalizing tonic composition having a greater hair loss prevention effect and hair revitalizing effect, and preventing dandruff or an itchy scalp.

Other objects and advantages of the present invention will be apparent from the following description.

In accordance with the present invention, there is provided a hair revitalizing tonic composition having an amine oxide formulated therein.

In accordance with the present invention, there is also provided a hair revitalizing tonic composition having an amine oxide and an anionic surfactant formulated therein.

The present invention is now described in detail.

The amine oxide usable in the hair revitalizing tonic composition of the present invention may include the following compounds:

(1) an amine oxide such as dimethylalkylamine oxide or dimethylalkenylamine oxide represented by the following formula (A):

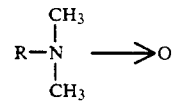

wherein R represents a straight or branched, saturated or unsaturated hydrocarbon group having 8 to 36 carbon atoms, preferably an alkyl group or an alkenyl group having 8 to 36 carbon atoms, preferably 12 to 28 carbon atoms;

(2) an amine oxide such as methyldialkylamine oxide or methyl-dialkenylamine oxide represented by the following formula (B):

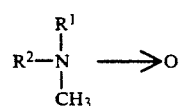

wherein $R^1$ and $R^2$ each represent a straight or branched, saturated or unsaturated hydrocarbon group having 6 to 36 carbon atoms, preferably an alkyl or alkenyl group having 6 to 36 carbon atoms, preferably 12 to 28 carbon atoms;

(3) an amine oxide such as dihydroxyethylalkylamine oxdie or dihydroxyethylalkenylamine oxide represented by the following formula (C):

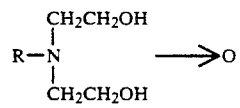

wherein R represents a straight or branched, saturated or unsaturated hydrocarbon group having 8 to 36 carbon atoms, preferably an alkyl or alkenyl group having 8 to 36 carbon atoms, preferably 12 to 28 carbon atoms;

(4) an amine oxide such an dimethylalkylpolyoxyethyleneamine oxide or dimethylalkenylpolyoxyethyleneamine oxide represented by the following formula (D):

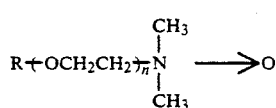

wherein R represents a straight or branched, saturated or unsaturated hydrocarbon group having 8 to 36 carbon atoms, preferably an alkyl group or an alkenyl group having 8 to 36 carbon atoms, preferably 12 to 28 carbon atoms, and n is an integer of 1 to 5.

In the present invention, these amine oxides can be used alone or in any mixture thereof.

In the present invention, the amount of the above amine oxide formulated may be from 0.0001 to 20% by weight of the total amount of the hair revitalizing tonic composition of the present invention. When the amounted formulated is less than 0.0001% by weight, a satisfactory revitalizing effect cannot be obtained, and an amount in excess of 20% by weight is not preferable from the aspect of preparation and/or skin irritation. The hair revitalizing tonic composition according to the present invention is not intended to be used for washing as the foaming during application can be a harmful factor, and therefore, a more preferable amount is 0.05 to 5% by weight.

This anionic surfactant usable in the hair revitalizing tonic composition according to the second embodiment of the present invention may include, for example, base materials for soaps; fatty acid soaps such as sodium laurate and sodium palmitate; higher alkyl sulfates such as sodium lauryl sulfate and potassium lauryl sulfate; alkyl ether sulfate salts such as triethanolamine polyoxyethylene (hereinafter abbreviated as POE) lauryl sulfate and POE sodium lauryl sulfate; higher fatty acid amide sulfonates such as N-myristoyl-N-methyltaurin sodium, coconut oil fatty acid methyltaurid sodium, and laurylmethyl-tauride sodium; phosphate esters such as sodium POE oleylether phosphate and POE stearyl ether phosphate; sulfosuccinates such as sodium di-2-ethylhexylsulfosuccinate, sodium monolauryol monoethanolamide polyoxyethylene sulfosuccinate, and sodium lauryl polypropylene glycol suflosuccinate; alkylbenzenesulfonates such as sodium linear dodeceylbenzene sulfonate and triethanolamine linear dodecylbezenesulfonate; N-acylglutamates such as monosodium N-lauroylglutamate, disodium N-stearoylglutamate, and monosodium N-myristoryl-L-glutamate; higher fatty acid ester sulfonates such as sodium hardened coconut oil fatty acid glycerine ester sulfate; sulfate oils such as Turkey red oil; POE alkyl ether carboxylic acids; POE alkylallyl ether carboxylates; α-olefin sulfonates; higher fatty acid ester sulfonates; secondary alcohol sulfates; higher fatty acid alkylolamide sulfate salts; sodium lauroyl monoethanolamide succinate; ditriethanolamine N-palmitoylasparate; casein sodium; and the like, and these anionic surfactants can be used alone or as any desired mixture of two or more thereof.

The formulation ratio of the amine oxide to the anionic surfactant in the hair revitalizing tonic composition according to the present invention is not particularly limited, but is preferably 20:1 to 1:5, more preferably 8:1 to 1:2, in terms of weight ratio. When the formulation ratio of the amine oxide to the anionic surfactant is outside the above-mentioned range, a satisfactory dandruff and itchy scalp prevention cannot be obtained. Preferably, the amine oxide content is 0.0001 to 20% by weight based upon the weight of the composition.

According to the present invention, an amine oxide or both an amine oxide and an anionic surfactant can be formulated in a conventional formulation of a hair cosmetics composition to prepare a desired hair revitalizing tonic composition. As such a formulation, for example, there may be included water, an alcohol (e.g., ethanol, isopropanol, preferably ethanol, hereinafter the same), a water-alcohol mixture (e.g., 20 to 99% by weight of an alcohol, the balance being water), an oil component, a water-oil component mixture (0.2 to 80% by weight of oil component, the balance being water), an alcohol-oil component mixture (0.2 to 80% of an oil component, the balance being alcohol), an water-alcohol-oil mixture (20 to 99% by weight of alcohol, 0.01 to 80% by weight of an oil component, the balance being water), a water-oil component-surfactant mixture (0.2 to 80% by weight of an oil component, 0.01 to 10% by weight of a surfactant, the balance being water), and a water-alcohol-oil component-surfactant mixture (20 to 99% by weight of an alcohol, 0.2 to 80% by weight of an oil component, 0.01 to 10% by weight of surfactant, balance being water). As the above oil component and the surfactant, any of those generally used in hair revitalizing tonic or cosmetic compositions of the prior art can be used. Examples of such oil components are olive oil, squalane, fluid paraffin, isopropyl myristate, higher fatty acids and higher alcohols. Examples of such surfactants are nonionic surfactants, anionic surfactants, amphoteric surfactants, cationic surfactants, and semipolar surfactants.

In the hair revitalizing tonic composition according to the present invention, in addition to the above essential components, general purpose components ordinarily used in hair revitalizing tonic compositions can be formulated, within a range which does not impair the effect of the present invention, including vitamins such as vitamin $B_6$, vitamin E and derivatives thereof, and biotin; hair generating agents or hair generating aids such as panthothenic acid and derivatives thereof, glycylrrhetic acid and derivatives thereof, nicotinic acid esters such as benzyl nicotinate, cyclosporins, carpronium chloride, cepharanthine, oxendolone, diazoxide, minoxidil, and ethynylesteradiol; antibacterial agents such as hinokitiol, hexachlorophen, phenol, benzalkonium chloride, cetylpyridinium chloride, undecylenic acid, trichlorocarbanilide, and bithionol; refrigerants such as menthol; drugs such as salicylic acid, zinc and derivatives, thereof, and lactic acid and alkyl esters thereof; organic acids such as citric acid; amino acids such as arginine; oil components such as olive oil, squalane, fluid paraffine, isopropyl myristate, higher fatty acids, and higher alcohols; polyhydric alcohols such as glycerine and propylene glycol; nonionic surfactants; cationic surfactants; perfumes; antioxidants; UV-ray absorbers; dyes; alcohols such as ethanol, benzyl alcohol, and isopropyl alcohol; water; humectants; and thickeners and the like.

The hair revitalizing tonic composition of the present invention can be in any preparation form, provided that it can be applied to the outer skin, such as a liquid, an emulsion, an ointment, a cream, a gel, or a spray, and can be used in such forms as a tonic, conditioner, or a scalp treatment.

The hair revitalizing tonic composition containing an amine oxide according to the present invention has an excellent hair loss prevention and hair revitalizing effect.

Also, the hair revitalizing tonic composition containing an amine oxide and an anionic surfactant has an excellent hair loss prevention, and hair revitalizing effect, and at the same time, has an excellent dandruff and itchy scalp prevention effect.

EXAMPLES

The present invention is described in more detail below by referring to Examples, which in no way limit the present invention. In the following Examples, the formulation amounts are by % by weight, and the effect testing methods and evaluation methods used in the Examples are as described below.

Hair Loss Prevention Effect Test

This effect was judged by the determining the change in the number of hairs lost during hair washing, before and after using the sample. Eight persons were test as a group for each of Examples 1 to 4 and for Comparative Example 1, and 4 persons were tested as a group for each of Examples 5 to 10. The test period was 6 months, in which the sample was not used for the first 2 months, and was used during last 4 months. During the period in which the sample was used, the sample was applied to the scalp twice a day, in an amount of 2 to 4 ml for each application. During the test period, the hair loss was determined by washing the hair every other day, and counting the total number of hairs lost each week. The numbers of hairs lost during each period is given by summarizing the data of the number of hairs lost during the 2 months for which the sample was not applied, multiplied by 8 to obtain a total, and the data of the number of hairs lost during the last 2 months of the 4 months during which the sample was applied, multiplied by 8 to obtain a total, in terms of the hair loss average value ± a standard deviation. The judgement of the effect was represented as follows, based on the difference in average values obtained in the respective periods.

++: Remarkable effect observed with number of hair lost being reduced by 70 or more;

+: Considerable effect observed with number of hairs lost being reduced by 40 or more;

±: Slight effect observed with number of hairs lost being reduced by 10 or more;

−: No effect observed with number of hairs lost being reduced by less than 10.

Hair Revitalizing Effect Test

To determine the hair revitalizing effect of the hair revitalizing tonic composition of the present invention, the trichogram test was carried out. Five persons were tested as a group for each of Examples 1 to 4 and for Comparative Example 1, and four persons were tested as group for each of Examples 5 to 10. The sample was applied for 3 months, during which period the sample was applied to the scalp twice a day, in an amount of 2 to 4 ml for each application. Immediately before application and immediately after application for 3 months, 50 hairs were removed from the parietal region of the scalp, the hair roots of the removed hair were observed under a microscope, and the root resting period ratio (%) was calculated from the form of the hair roots. The hair revitalizing effect of each sample was based on a comparison of the increase or decrease in the resting period ratio before and after application of the sample.

Dandruff, Itchy Scalp Prevention Effect Test

Four persons were tested as a group for each of the Examples and Comparative examples. The sample was applied for 3 months, during which period the hair was washed once per day with the same shampoo, not having a drug added thereto, and the test sample was applied to the scalp twice per day, in an amount of 2 to 4 ml for each application. On completion of the test period, the dandruff on the head was collected by an aspirating device from the persons tested, and the amount of protein in the dandruff was measured.

Also, on completion of the test period, itching of the scalps of the persons tested was examined, and the extent of the itching was represented according to the following scores.

Strong itch ... 3
Some itch ... 2
Slight itch ... 1
No itch ... 0

EXAMPLES 1–10 AND COMPARATIVE EXAMPLE 1

The formulations of Examples 1–10 and Comparative Example 1 are shown in Tables 1 and 2, the results of the hair loss prevention effect test of Examples 1–10 and Comparative Example 1 are shown in Tables 3 to 5, the results of the hair revitalizing effect test of Examples 1–10 and Comparative Example 1 are shown in Tables 6 and 7, and the results of dandruff and itchy scalp prevention effect test of Examples 1, 8, 9, 10 and Comparative Example 1 are shown in Table 8.

TABLE 1

| Component | Example 1 | Example 2 | Example 3 | Example 4 | Comparative Example 1 |
|---|---|---|---|---|---|
| Dimethyllaurylamine oxide | 0.2 | — | — | — | — |
| Methyldioctylamine oxide | — | 0.008 | — | — | — |
| Dihydroxyethylstearylamine oxide | — | — | 0.05 | — | — |
| Lauryl POE (3 mole addition) dimethylamine oxide | — | — | — | 1.0 | — |
| 95% Ethanol | 75.0 | 75.0 | 75.0 | 75.0 | 75.0 |
| Purified water | balance | balance | balance | balance | balance |

TABLE 2

| Component | Example 5 | Example 6 | Example 7 | Example 8 | Example 9 | Example 10 |
|---|---|---|---|---|---|---|
| Dimethyllaurylamine oxide | — | — | — | 0.2 | — | 0.2 |
| Dimethyloleylamine oxide | 1.0 | — | — | — | 0.2 | — |
| Dimethylisostearylamine oxide | — | 0.3 | — | — | — | — |
| Decylmethyloctylamine oxide | — | — | 0.5 | — | — | — |
| Sodium lauryl sulfate | — | — | — | 0.06 | — | — |
| Coconut oil fatty acid methyltauride sodium | — | — | — | — | 0.1 | — |
| Monosodium N-lauroyl-glutamate | — | — | — | — | — | 0.14 |
| 95% Ethanol | 75.0 | 75.0 | 75.0 | 75.0 | 75.0 | 75.0 |
| Purified water | balance | balance | balance | balance | balance | balance |

TABLE 3

| Group | No. of person tested | Number of hairs lost — No application period | Number of hairs lost — Application period | Judgement |
|---|---|---|---|---|
| Example 1 | 1 | 289 ± 45 | 233 ± 55 | + |
| | 2 | 500 ± 54 | 378 ± 70 | ++ |
| | 3 | 220 ± 41 | 217 ± 22 | − |
| | 4 | 473 ± 54 | 391 ± 62 | ++ |
| | 5 | 351 ± 21 | 289 ± 33 | + |
| | 6 | 255 ± 52 | 224 ± 39 | ± |
| | 7 | 117 ± 36 | 113 ± 32 | − |
| | 8 | 357 ± 53 | 302 ± 49 | + |
| Example 2 | 1 | 355 ± 38 | 246 ± 50 | ++ |
| | 2 | 433 ± 40 | 382 ± 35 | + |
| | 3 | 458 ± 56 | 402 ± 46 | + |
| | 4 | 313 ± 34 | 332 ± 45 | − |
| | 5 | 375 ± 65 | 347 ± 62 | ± |
| | 6 | 122 ± 15 | 126 ± 14 | − |
| | 7 | 497 ± 75 | 476 ± 82 | ± |
| | 8 | 231 ± 42 | 188 ± 33 | + |
| Example 3 | 1 | 258 ± 41 | 252 ± 38 | − |
| | 2 | 433 ± 41 | 350 ± 62 | ++ |
| | 3 | 501 ± 53 | 455 ± 47 | + |
| | 4 | 161 ± 57 | 120 ± 42 | + |
| | 5 | 145 ± 22 | 138 ± 26 | − |
| | 6 | 476 ± 76 | 365 ± 52 | ++ |
| | 7 | 512 ± 43 | 363 ± 77 | ++ |
| | 8 | 223 ± 22 | 195 ± 24 | ± |

TABLE 4

| Group | No. of person tested | Number of hairs lost — No application period | Number of hairs lost — Application period | Judgement |
|---|---|---|---|---|
| Example 4 | 1 | 126 ± 12 | 128 ± 15 | − |
|  | 2 | 468 ± 42 | 342 ± 54 | ++ |
|  | 3 | 313 ± 41 | 302 ± 48 | ± |
|  | 4 | 500 ± 56 | 407 ± 62 | ++ |
|  | 5 | 309 ± 51 | 268 ± 45 | + |
|  | 6 | 254 ± 42 | 241 ± 38 | ± |
|  | 7 | 497 ± 32 | 415 ± 39 | ++ |
|  | 8 | 186 ± 21 | 163 ± 26 | ± |
| Comparative Example 1 | 1 | 421 ± 69 | 433 ± 64 | − |
|  | 2 | 423 ± 36 | 417 ± 42 | − |
|  | 3 | 346 ± 45 | 334 ± 50 | ± |
|  | 4 | 113 ± 21 | 121 ± 18 | − |
|  | 5 | 277 ± 69 | 260 ± 53 | ± |
|  | 6 | 189 ± 21 | 198 ± 23 | − |
|  | 7 | 290 ± 36 | 291 ± 43 | − |
|  | 8 | 567 ± 77 | 531 ± 83 | + |

TABLE 5

| Group | No. of person tested | Number of hairs lost — No application period | Number of hairs lost — Application period | Judgement |
|---|---|---|---|---|
| Example 5 | 1 | 482 ± 55 | 378 ± 70 | ++ |
|  | 2 | 501 ± 54 | 366 ± 45 | ++ |
|  | 3 | 186 ± 52 | 143 ± 22 | + |
|  | 4 | 357 ± 53 | 229 ± 36 | ++ |
| Example 6 | 1 | 443 ± 41 | 323 ± 40 | ++ |
|  | 2 | 313 ± 34 | 299 ± 23 | ± |
|  | 3 | 122 ± 15 | 126 ± 14 | − |
|  | 4 | 259 ± 52 | 188 ± 33 | ++ |
| Example 7 | 1 | 443 ± 41 | 360 ± 62 | ++ |
|  | 2 | 261 ± 57 | 220 ± 42 | + |
|  | 3 | 478 ± 76 | 367 ± 62 | ++ |
|  | 4 | 223 ± 18 | 196 ± 20 | ± |
| Example 8 | 1 | 123 ± 11 | 122 ± 13 | − |
|  | 2 | 463 ± 54 | 371 ± 62 | ++ |
|  | 3 | 155 ± 22 | 124 ± 29 | ± |
|  | 4 | 357 ± 53 | 251 ± 26 | ++ |
| Example 9 | 1 | 333 ± 31 | 282 ± 25 | + |
|  | 2 | 313 ± 34 | 262 ± 29 | + |
|  | 3 | 122 ± 15 | 111 ± 14 | ± |
|  | 4 | 231 ± 42 | 148 ± 23 | ++ |
| Example 10 | 1 | 322 ± 31 | 241 ± 32 | ++ |
|  | 2 | 161 ± 57 | 155 ± 42 | − |
|  | 3 | 555 ± 45 | 412 ± 52 | ++ |
|  | 4 | 213 ± 22 | 195 ± 23 | ± |

TABLE 6

| Group | No. of person tested | Hair root resting ratio (%) — Immediately before application | Hair root resting ratio (%) — After application | Judgement |
|---|---|---|---|---|
| Example 1 | 1 | 24.2 | 21.0 | ± |
|  | 2 | 42.0 | 29.6 | + |
|  | 3 | 12.0 | 12.7 | − |
|  | 4 | 35.7 | 14.1 | + |
|  | 5 | 33.4 | 25.2 | + |
| Example 2 | 1 | 36.1 | 36.9 | − |
|  | 2 | 41.8 | 27.2 | + |
|  | 3 | 33.9 | 29.8 | ± |
|  | 4 | 21.1 | 18.2 | ± |
|  | 5 | 25.3 | 14.0 | + |
| Example 3 | 1 | 17.1 | 15.3 | ± |
|  | 2 | 40.1 | 31.0 | + |
|  | 3 | 19.8 | 16.9 | ± |
|  | 4 | 36.9 | 25.3 | + |
|  | 5 | 28.6 | 21.2 | + |
| Example 4 | 1 | 22.9 | 20.8 | ± |
|  | 2 | 38.8 | 31.1 | + |
|  | 3 | 43.8 | 27.2 | + |
|  | 4 | 25.3 | 20.1 | + |
|  | 5 | 14.2 | 15.0 | − |
| Comparative Example 1 | 1 | 43.2 | 41.8 | − |
|  | 2 | 14.0 | 15.7 | − |
|  | 3 | 21.2 | 21.1 | − |
|  | 4 | 32.9 | 27.3 | ± |
|  | 5 | 38.0 | 40.6 | − |

(+ remarkable effect, ± weak effect, − no effect)

TABLE 7

| Group | No. of person tested | Hair root resting ratio (%) — Immediately before application | Hair root resting ratio (%) — After application | Judgement |
|---|---|---|---|---|
| Example 5 | 1 | 25.1 | 19.2 | + |
|  | 2 | 16.2 | 13.6 | ± |
|  | 3 | 12.0 | 12.5 | − |
|  | 4 | 28.6 | 11.1 | + |
| Example 6 | 1 | 32.1 | 29.1 | ± |
|  | 2 | 29.3 | 20.1 | + |
|  | 3 | 18.3 | 15.5 | ± |
|  | 4 | 20.9 | 11.2 | + |
| Example 7 | 1 | 25.3 | 14.6 | + |
|  | 2 | 40.9 | 30.0 | + |
|  | 3 | 18.8 | 17.0 | ± |
|  | 4 | 32.6 | 24.6 | + |
| Example 8 | 1 | 22.0 | 19.6 | ± |
|  | 2 | 44.0 | 30.1 | + |
|  | 3 | 28.3 | 20.7 | + |
|  | 4 | 25.3 | 19.9 | + |
| Example 9 | 1 | 17.0 | 15.1 | ± |
|  | 2 | 40.1 | 32.0 | + |
|  | 3 | 24.3 | 18.9 | + |
|  | 4 | 35.9 | 29.9 | + |
| Example 10 | 1 | 22.2 | 19.4 | ± |
|  | 2 | 37.8 | 30.1 | + |
|  | 3 | 44.8 | 26.2 | + |
|  | 4 | 15.2 | 14.9 | − |

(+ remarkable effect, ± weak effect, − no effect)

TABLE 8

| Group | Average amount of dandruff (mg) | Itch (average score) |
|---|---|---|
| Example 1 | 14.62 | 1.5 |
| Example 8 | 6.93 | 0.5 |
| Example 9 | 5.31 | 0.25 |
| Example 10 | 6.65 | 0.25 |
| Comparative Example 1 | 19.11 | 2.0 |

As apparent from the results shown in Table 3 to 7, (1) the hair revitalizing tonic composition having an amine oxide formulated therein and (2) the hair revitalizing tonic composition having an amine oxide and an anionic surfactant formulated therein were found to have an excellent hair loss prevention effect and hair revitalizing effect.

Also, as apparent from the result shown in Table 8, the hair revitalizing tonic composition having an amine oxide and an anionic surfactant formulated therein was found to have an excellent dandruff and itchy scalp prevention effect.

EXAMPLE 11

A lotion comprising the following composition was prepared.

| Ingredient | Part |
| --- | --- |
| 95% Ethanol | 50.0 |
| Dimethyllaurylamine oxide | 0.2 |
| Sodium Lauryl sulfate | 0.06 |
| Hydrogenated castor oil ethylene oxide (40 mole) adduct | 0.5 |
| Purified water | Balance |
| Perfume and dye | q.s. |

(Preparation Methods)

In 95% ethanol were dissolved hydrogenated castor oil ethylene oxide (40 mole) adduct, and a perfume, and then purified water was added followed by an addition of dimethyllaurylamine oxide, sodium lauryl sulfate, and a dye, and the mixture was dissolved while stirring to obtain a transparent liquid lotion.

EXAMPLE 12

A lotion comprising the following composition was prepared.

| Ingredient | Part |
| --- | --- |
| 95% Ethanol | 90.0 |
| Lauroyl POE (3 mole addition) dimethylamine oxide | 3.0 |
| Sodium lauryl sulfate | 1.0 |
| Hydrogenated castor oil ethylene oxide (40 mole) adduct | 0.5 |
| Purified water | Balance |
| Perfume and dye | q.s. |

(Preparation Methods)

In 95% ethanol were dissolved hydrogenated castor oil ethylene oxide (40 mole) adduct, and a perfume, and then purified water was added followed by an addition of lauryl POE (3 mole addition) dimethylamine oxide, sodium lauryl sulfate, and a dye, and the mixture was dissolved while stirring to obtain a transparent liquid lotion.

EXAMPLE 13

| Ingredient | Part |
| --- | --- |
| (A phase) | |
| Fluid paraffin | 5.0 |
| Cetostearyl alcohol | 5.5 |
| Glycerine monostearate | 3.0 |
| Polyoxyethylene (20 mole addition) 2-octyldodecyl ether | 3.0 |
| Vitamin E acetate | 0.05 |
| Propylparaben | 0.3 |
| Perfume | 0.05 |
| (B phase) | |
| Glycerine | 7.0 |
| Dipropylene glycol | 20.0 |
| Polyethylene glycol 4000 | 5.0 |
| Sodium hexmetaphosphate | 0.005 |
| Purified water | Balance |
| Dimethylcetylamine oxide | 12.0 |

(Preparation Method)

The A phase and the B phase were respectively dissolved by heating, mixed, and then emulsified by a homomixer to obtain a hair revitalizing tonic composition in the form of an ointment.

EXAMPLE 14

| Ingredient | Part |
| --- | --- |
| (A phase) | |
| Cetanol | 2.0 |
| Petrolatum | 5.0 |
| Squalane | 10.0 |
| Polyoxyethylene (10 mole addition) monostearate | 2.0 |
| Sorbitane monooleate | 1.0 |
| Dimethylstearylamine oxide | 1.0 |
| Perfume | 0.1 |
| (B phase) | |
| Glycerine | 10.0 |
| 20% Gluconic acid chlohexidine solution | 0.1 |
| Purified water | Balance |

(Preparation Method)

The A phase and the B phase were respectively dissolved by heating, were mixed, and were emulsified by a homomixer to obtain a hair revitalizing tonic composition in the form of an emulsion.

Examples 11 to 14 were found to have an excellent hair loss prevention effect and hair revitalizing tonic effect. Also, Examples 11 and 12 further had an excellent dandruff and itchy scalp prevention effect.

EXAMPLE 15

A lotion comprising the following composition was prepared.

| Ingredient | Part |
| --- | --- |
| 95% Ethanol | 80.0 |
| N,N-Dimethyl-2-hexyldecylamine oxide | 2.0 |
| Sodium N-lauroyl glutamate | 0.8 |
| Hydrogenated castor oil ethylene oxide (40 mole) adduct | 0.5 |
| Glycerol | 1.0 |
| Vitamin E acetate | 0.1 |
| Citric acid | q.s. |
| Sodium citrate | q.s. |
| EDTA.2Na | q.s. |
| Purified water | Balance |
| Perfume | q.s. |

(Preparation Method)

In 95% ethanol were dissolved N,N-dimethyl-2-hexyldecylamine oxide, hydrogenated castor oil ethylene oxide (40 mole) adduct and perfume, and the solution was added to water containing glycerol, citric acid, sodium citrate and EDTA.2Na dissolved therein, followed by an addition of vitamin E acetate and sodium N-lauroyl glutamate. The mixture was dissolved while stirring to obtain a transparent liquid lotion.

EXAMPLE 16

A lotion comprising the following composition was prepared.

| Ingredient | Part |
| --- | --- |
| 95% Ethanol | 90.0 |
| N,N-dimethyl-2-decyltetradecylamine oxide | 1.0 |
| Sodium dodecyl sulfate | 0.4 |
| Hydrogenated castor oil | 1.0 |

-continued

| Ingredient | Part |
|---|---|
| ethylene oxide (60 mole) adduct | |
| Citric acid | q.s. |
| Sodium citrate | q.s. |
| EDTA.2Na | q.s. |
| Purified water | Balance |
| Perfume | q.s. |

(Preparation Method)

In 95% ethanol were dissolved N,N-dimethyl-2-decyltetradecylamine oxide, hydrogenated castor oil ethylene oxide (60 mole) adduct and perfume, and the solution was added to the purified water containing citric acid, sodium citrate and EDTA.2Na dissolved therein, followed by an addition of sodium dodecylsulfate. The mixture was dissolved while stirring to obtain a transparent liquid lotion.

EXAMPLE 17

A lotion comprising the following composition was prepared.

| Ingredient | Part |
|---|---|
| N,N-Dimethyl-2-tetradecyl-hexadecylamin oxide | 1.5 |
| Glycerol | 2.0 |
| Hydrogenated castor oil ethylene oxide (40 mole) adduct | 1.0 |
| Perfume | q.s. |
| 95% Ethanol | Balance |

(Preparation Method)

To 95% ethanol were added N,N-dimethyl-2-tetradecylhexadecylamine oxide, glycerol, hydrogenated castor oil ethylene oxide (40 mole) adduct and perfume, followed by dissolving, while stirring, to obtain a transparent liquid lotion.

Examples 16 and 17 were found to have, in addition to a good hair loss prevention effect and hair revitalizing effect, an excellent applicability to the hair and an excellent characteristic capable of giving a glossy, moist, and soft feeling to the hair.

We claim:

1. A composition for revitalizing hair and for preventing dandruff and itchy scalp comprising 0.0001 to 20% by weight of an amine oxide, and an anionic surfactant, the weight ratio of the amino oxide to the anionic surfactant ranging from 20:1 to 1:5, the amine oxide comprising at least one member selected from the group consisting of (A), (B), (C) and (D) of the formulas

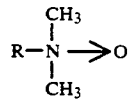

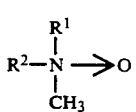

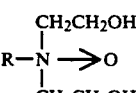

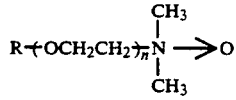

in which

R is a hydrogen radical having 8 to 36 carbon atoms,
$R^1$ and $R^2$ each independently is a hydrocarbon radical having 6 to 36 carbon atoms, at least one of R, $R^1$ and $R^2$ having 24 to 36 carbon atoms, and n is an integer from 1 to 5, the anionic surfactant comprising at least one member selected from the group consisting of a fatty acid soap, higher alkyl sulfate, alkyl ether sulfate salt, higher fatty acid amide sulfonate, phosphate ester, sulfosuccinate, alkylbenzenesulfonate, N-acylglutamate, higher fatty acid ester sulfonate, sulfate oil, POE alkyl ether carboxylic acid, POE alkylallyl ether carboxylate, α-olefin sulfonate, higher fatty acid ester sulfonate, secondary alcohol sulfate, higher fatty acid alkylolamide sulfate salt, sodium lauroyl monoethanolamide succinate, ditriethanolamine N-palmitoylaspartate and casein sodium.

2. A composition according to claim 1, containing the amine oxide in from 0.05 to 5% by weight.

3. A composition according to claim 1, wherein the ratio of the amine oxide to the anionic surfactant is from 8:1 to 1:2.

4. A method for revitalizing hair and for preventing dandruff and itchy scalp, which comprises applying to the scalp and leaving thereon a hair revitalizing effective amount of a composition according to claim 1.

5. A method for revitalizing hair and for preventing dandruff and itchy scalp, which comprises applying to the scalp and leaving thereon a hair revitalizing effective amount of a composition according to claim 2.

6. A method for revitalizing hair and for preventing dandruff and itchy scalp, which comprises applying to the scalp and leaving thereon a hair revitalizing effective amount of a composition according to claim 3.

* * * * *